United States Patent [19]

Böcker et al.

[11] 4,086,346
[45] Apr. 25, 1978

[54] PREPARATION OF MELT-SPRAYED SPHERICAL PHENACETIN GRANULES

[75] Inventors: Ernst Böcker; Wolfgang Kracht; Roland Rupp, all of Leverkusen; Erhard Schellmann, Cologne; Viktor Trescher; Martin Ullrich, both of Leverkusen, all of Germany

[73] Assignee: Bayer Aktiengesellschaft, Germany

[21] Appl. No.: 720,650

[22] Filed: Sep. 7, 1976

Related U.S. Application Data

[63] Continuation-in-part of Ser. No. 564,168, Apr. 1, 1975, abandoned, and Ser. No. 564,169, Apr. 1, 1975, abandoned.

[30] Foreign Application Priority Data

Apr. 6, 1974 Germany .............................. 2416903
Apr. 6, 1974 Germany .............................. 2416904

[51] Int. Cl.$^2$ ...................... A61K 9/16; A61K 31/52; A61K 31/165
[52] U.S. Cl. ........................................ 424/253; 264/5; 264/13; 264/109; 264/117; 264/123; 264/319; 264/345; 264/349; 424/324
[58] Field of Search ...................... 264/5, 13, 109–117, 264/123, 319, 345, 349; 424/14, 253, 324

[56] References Cited

U.S. PATENT DOCUMENTS

| | | | |
|---|---|---|---|
| 3,341,415 | 9/1967 | Scott | 264/13 |
| 3,388,196 | 6/1968 | Farrell | 264/176 |
| 3,439,633 | 4/1969 | Pawlak et al. | 264/13 |
| 3,615,142 | 10/1971 | Dahlbom | 264/13 |
| 3,698,844 | 10/1972 | Grimm | 425/144 |

OTHER PUBLICATIONS

Zaputryaev et al., (1969), Transl. of "The Preparation of Phenacetin Tablets by using Liquefaction", Chem. Abstr. 71 #94721B (1969) of Khimoko-Farmatsevticheskiizhurnal 3(5): 5–54 (1969).

Zaputryaev et al., (1970), Transl. of "Use of Fusion for Preparing Two-Component Tablets Containing Sodium Salts of Organic Acids", Chem. Abstr. 73, #133970v (1970) of Khim-Farmzh 418), 23–26 (1970).

Goodhart et al., J. Pharm. Sci. 62 (1): 133–136 Jan. 1973, Design and Use of a Laboratory Extruder for Pharmaceutical Granulations.

Malinowski et al., J. Pharm. Sci. 63(2): 285–288, Feb. 1974, Effect of Spheronization Process Variables on Selected Tablet Properties.

Jalal et al., J. Pharm. Sci. 61(9): 1466–1468, Sep. 1972, Tablet Granulations Composed of Spherical-Shaped Particles.

Woodruff et al., J. Pharm. Sci. 61(5): 787–790, May 1972, "Effect of Processing Variables on Particles Obtained by Extrusion-Spheronization Processing".

Perry et al., Chemical Engineers Handbook, McGraw-Hill (1973), pp. 10-4-10-10, McKelvey Polymer Processing, Wiley, N.Y. 1967, pp. 288–297.

Weast et al., Handbook of Chem. & Physics, 50th Ed., (1969), Chem. Rubber Cleve. O pp. C74, C78.

Primary Examiner—Shep K. Rose
Attorney, Agent, or Firm—Jacobs & Jacobs

[57] ABSTRACT

Substantially spherical granules of phenacetin are prepared by spraying liquid phenacetin which has been melted without decomposition by means of rapid passage through a melting device in which superheating is minimized. The resultant melt-sprayed granules are superior to crystalline phenacetin in the formulation of pharmaceutical tablets.

15 Claims, 6 Drawing Figures

FIG. 3A  ⊢—⊣ 50 μm
FIG. 3B  ⊢—⊣ 5 μm
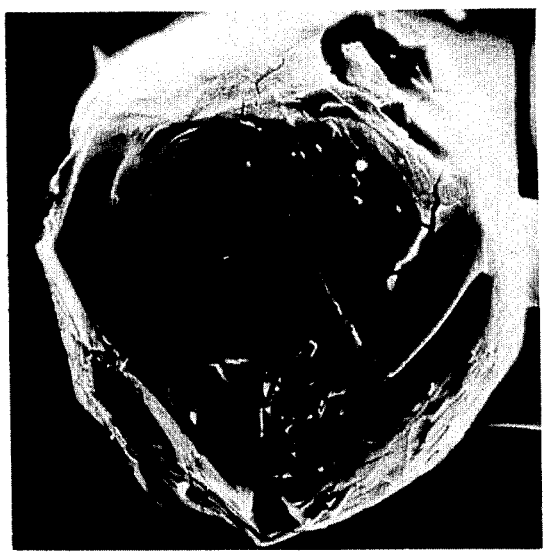
FIG. 4A  ⊢—⊣ 50 μm
FIG. 4B  ⊢—⊣ 5 μm

PREPARATION OF MELT-SPRAYED SPHERICAL PHENACETIN GRANULES

CROSS-REFERENCE

This is a continuation-in-part of Ser. Nos. 564,168 and 564,169, both filed Apr. 1, 1975, both now abandoned.

DETAILED DESCRIPTION

The present invention is concerned with melt-sprayed spherical phenacetin granules, their preparation and the formation of tablets therefrom.

A substance can be tableted directly if it can be compressed into tablets of good mechanical strength without the inerposition of customary granulating processes; i.e., the formation by intempted crystallization or precipitation of a finely crystalline granular powder. The ability to undergo direct compression is of importance in the production of tablets since a substance which is capable of being tableted directly should produce tablets of good mechanical properties even when tableted with auxiliaries on high speed tableting machines.

There are however few substances which can be compressed into tablets without prior granulation. These include ammonium bromide, ammonium chloride, ammonium iodide, potassium bromide, potassium chlorate, potassium chloride, potassium bichromate, potassium permanganate, sodium bromide, sodium chloride, sodium cyclamate, sodium thiosulphate, sodium citrate, hexamethylenetetramine, ipecacuanha powder and licorice extract [see W. A. Ritschel: "Die Tablette", Ed. Cantor Verlag, Aulendorf, 1966, page 217 and 218]. Other substances can be rendered directly compressible and tableted by means of additives. These include, inter alia, potassium aluminium sulphate, potassium aluminium iodide, potassium aluminium nitrate, calcium chloride, sodium tetraborate, aminophenazone, acetylsalicyclic acid, chloral hydrate, camphor monobromate, pancreatin, pepsin and phenolphthalein.

A majority of other biologically active substances must be subjected to known granulating techniques in order to produce a finely crystalline granular powder capable of being compressed into tablets.

Phenacetin is known to be a substance which is distinctly difficult to convert to tablets. Thus attempts to tablet crystalline phenacetin having varied shape and particle size distribution results in tablets of poor mechanical strength which exhibit extensive capping and layer formation [see, e.g. Jaffe et al., J. Am. Pharm. Ass., 48, 26–29 (1959); Blaey et al., Pharm. Ind., 33, 897–900 (1971)]. To prepare suitable tablets from phenacetin, it has been necessary to granulate crystalline material having a particle size of 100 to 600 $\mu$m or to granulate material which has been ground to a particle size of 20 to 60 $\mu$m.

The production of phenacetin tablets can be produced by moist granulation as described in the British Pharmaceutical Codex of 1968. An auxiliary, such as sugar or starch, is admixed to the crystalline phenacetin powder and the mixture is moistened with an aqueous or alcoholic binder solution, such as starch, gluten, gelatin or sugar solution and then granulated. Thereafter, disintegrating agents and lubricants are admixed to the dried granules. After these expensive mixing, granulating and drying processes have been carried out, the thus treated phenacetin can then be compressed to give tablets.

F. Biedenbach, in Pharmaz. Ztg. 103, 104, 1958 similarly describes a preliminary treatment with polyvinyl pyrrolidone to convert phenacetin into crystalline granules which can be tableted.

It has now been found that melt-sprayed, substantially noncrystalline, phenacetin granules which are spherical in configuration have improved compressibility and in fact can be tableted directly by compressing the granules.

In this specification the word "tablet" means a compressed body which is composed of a plurality of discrete particles, and includes pills, lozenges and dragee cores. "Phenacetin" includes simple substituted derivatives of phenactin. Tablets prepared from melt-sprayed spherical phenacetin granules have improved physical properties compared with conventional phenacetin tablets.

It is surprising that the phenacetin granules produced in accordance with the present invention exhibit such improved properties. According to the state of the art, it was not to be expected that an active compound in a spherical form would be easier to convert to tablets than an active compound in a crystalline form. Thus the literature contains very little experimentally verified information on the influence of particle geometry on compacting behavior. For pharmaceutical substances, apparently only the tableting behavior of crystalline and spherically spray-dried lactose has been studied. Indeed it has been suggested that the absence of a crystalline structure reduces the prospects of direct tableting [see, e.g., Enzian, Pharm. Acta Helv. 47, 323 (1972)]. Rounded crystal shapes, on the other hand, while showing better flow properties, at the same time reduce the hardness of the tablets so that irregular and sharp-edged crystals, coupled with relatively large crystal size, have been suggested as being necessary to obtain, on compression, a branched and multi-crosslinked tablet lattice which is rich in internal jagged points and spikes and therefore mechanically resistant. Hüttenrauch et al., Die Pharmazie, 23 475 (1968).

It has also been found that particles of potassium chloride having a rounded shape and a lower particle size distribution exhibit poorer compressive property than crystalline particles. [See, Lazarus et al., J. Pharm. Sci. 55, 1121–1127 (1966)].

The phenacetin granules of this invention are generally spherical in shape and are produced by melting the crystalline phenacetin, preferably in a special multi-screw extruder as described hereafter, and subsequently spraying the melt in a gaseous or liquid medium.

In the drawings,

FIGS. 3A–3B are scanning electron microscopic photographs of a commercial phenacetin crystal and FIGS. 4A–4B are corresponding scanning electron microscopic photographs of a spherical granule according to the invention, respectively.

Figure 1:
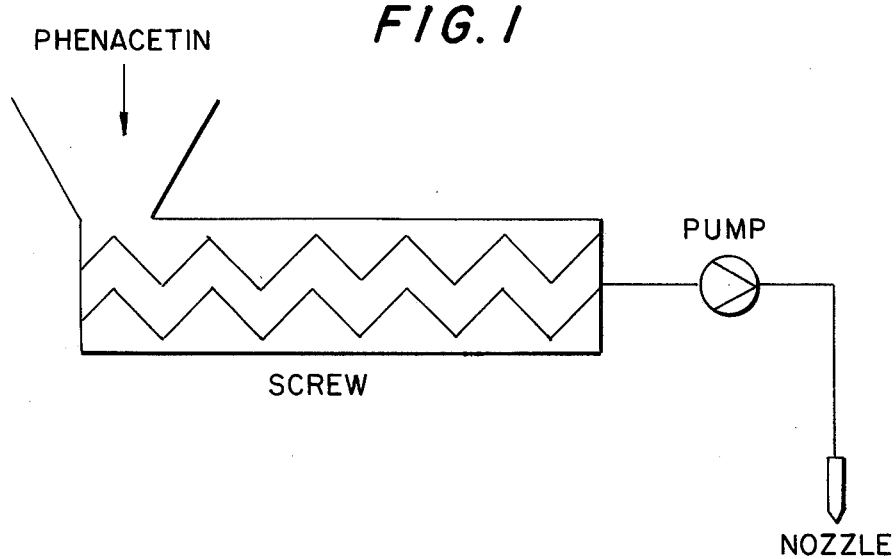
FIG. 1 is a schematic presentation of the manufacturing elements utilized in the process and FIG. 2 is a schematic cross section of the melting device.
Figure 2:
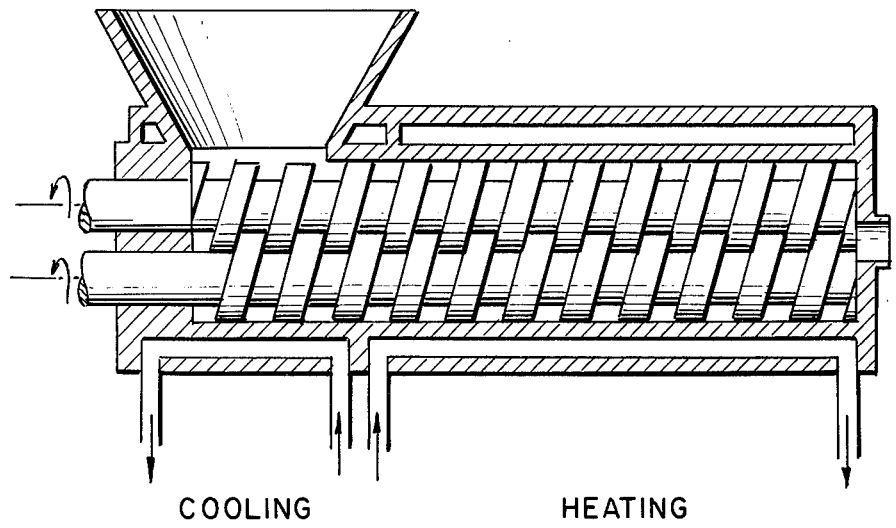

The phenacetin granules which can be used according to the invention preferably comprise at least 80% by weight of particles of size 20 – 500 $\mu$m.

The phenacetin granules have good flow properties and do not tend to acquire an excessive electrostatic charge in the way that the previously commercially available material does. The granules can therefore be compressed into tablets either as a single substance or in combination with further active compounds, and together with pharmaceutically acceptable excipients.

The ability of these granules to be compressed directly is of significant theoretical interest since it reflects the improved compressibility of the material. In practice such a tablet demonstrates insufficient disintegration to be of much therapeutic value.

Typical pharmaceutical excipients or auxiliaries include (a) fillers and extenders, as for example, edible carbohydrates such as starches, lactose, sucrose or glucose, mannitol and silica, (b) binders, such as for example, carboxymethylcellulose, alginates, gelatine, polyvinylpyrrolidone, lactose, glucose, sucrose, mannitol, calcium carbonate, calcium phosphate, polyethylene glycol, polyethylene oxides, cellulose, methylcellulose, hydroxyethylcellulose, amylose, pectins and sodium amylopectin glycollate, (c) humectants, such as for example, glycerol, (d) disintegrating agents, such as for example, agar-agar, calcium carbonate, sodium bicarbonate, starches, silicas, methylcellulose, alginic acid, alginates, formaldehyde-casein, pectins, magnesium aluminium silicates, sodium bicarbonate, calcium carbonate, magnesium oxide and sodium amylopectin glycollate, (e) sustained release agents, such as for example, paraffin, (f) absorption enhancing agents, such as for example, quaternary ammonium compounds, (g) wetting agents, such as for example, cetyl alcohol and glycerol monostearate, (h) adsorbents, such as for example, kaolin and bentonite and (i) lubricants, for example talc, calcium stearate, magnesium stearate and solid polyethylene glycols. Mixtures of these materials can of course be present. Furthermore, anti-static agents, dyestuffs and flavoring agents, such as for example, aromas and sweeteners, can also be added to the tablet mixture.

The present invention includes a process for the preparation of these spherical phenacetin granules from the melt phase, and a device for carrying out the process.

It is well known that molten organic materials can be converted into granules by passing the molten material through a single nozzle, twin nozzle, or spinning disc atomiser and allowing subsequent solidification in a gas or a liquid; see, e.g. W. Boretzky, in "Fette-Seifen-Anstrichmittel," No. 4, 1967, pp. 263–268 and G. Matz "Kristallisation in der Verfahrenstechnik" Springer 1957, pp 284–291. These processes are preferably carried out with materials which are not sensitive to heat. Thus, W. Boretzky reports that stearic acids, paraffins and synthetic resins can be granulated in this way.

This procedure is unsuitable for heat-sensitive substances since these tend to discolor and decompose on heating to, or above, their melting points. Previously, such substances have been processed in the melt phase without degradation only if suitable reducing agents were added. German Offenlegungsschrift No. 1,617,933 discloses for example that pharmaceutically active compounds can be fused without decomposition if mixed with reducing agents, such as aqueous hydrazine solutions or ammonium formate solutions.

In the case of medicaments such as phenacetin, however, any such reducing agents which are used in the preparation of granules must be completely removed in order to meet purity requirements. The latter process is therefore disadvantageous in that pure active compound is contaminated in order to fuse it, and a further purification step is thus necessary.

In accordance with this invention, it has been found that phenacetic granules can be prepared from molten phenacetin without reducing agents. Broadly, the phenacetin is melted, while preventing local superheating, to temperatures more than 15° F, preferably 10° C, above its melting point, and subsequently atomized, the phenacetin being maintained in a molten condition for a period not longer than 20 minutes, preferably not more than 10 minutes, prior to atomization.

More specifically, crystalline phenacetin is fused, without addition of a reducing agent or other auxiliary, in a continuously operating melting device which provides a low residence time and a narrow residence time spectrum, and subsequently atomizing the molten phenacetin. The melting device has heated surfaces maintained at temperatures of from 150° to 300° C and preferably comprises a plurality of intermeshing self-cleaning screws.

Although it has been reported that phenacetin can be heated above its melting point without decomposition [see Zaputriaev et al., *Khim. Farm. Zh.*, 3. No. 5, 1969, pp 51–54], according to Offenlegungsschrift No. 1,617,933, phenacetin decomposes even near the melting point if no suitable reducing agent is present. It was thus surprising that phenacetin which has been reported as being heat-sensitive, is not discolored or decomposed in a melting device having wall temperatures more than 100° C above the melting point.

The melting device used is preferably a heated intermeshing and self-cleaning multi-screw device with a narrow residence time spectrum and little play between both the screw crests and housing, and the screw flanks. A twin-screw device in which the screws rotate in the same direction and the play, relative to the diameter of one of the screws, is preferably from about $4 \times 10^{-3}$ to about $30 \times 10^{-3}$ is particularly suitable for gently melting the material. Such a twin-screw device was high heat transfer indices because of its particularly intense mixing effect, and therefore has a small volume filled with product. Additionally, because of its self-cleaning kinematics, deviations from the means residence time, which in any case is very short, are only slight. For example, the mean residence time is desirably no longer than ten minutes, and the total residence time is desirably no more than 20 minutes.

The intake zone of this melting screw should preferably be cooled to prevent difficult to handle pasty states of the material, formed by premature incipient melting, from hindering the flow of the crystalline phenacetin powder in the hopper zone. This intake zone is followed, in the feed direction, by a sealed, externally heated housing zone. Here, the powder is warmed to the melting point and undergoes intense forced convection. It then passes through a melting zone in which the consistency of the powder changes via pasty states to a mobile melt. It is particularly because of these states of the material, which are difficult to handle, that the use of the screw system described is of advantage. The screw shafts themselves can also be heated, in addition to the external heating of the housing, which has been mentioned.

The twin screw mentioned makes it possible to use very large temperature differences between the heating medium and the phenacetin without the latter issuing from the screw at temperatures which, on average, are more than 2° to 3° C above the melting point and without local superheating of the phenacetin to temperatures more than 10° C above its melting point. With a view to a short residence time and slight heat exposure, it is desirable to locate the end of the melting zone as close as possible to the exit from the screw. The melt issuing from the screw is fed, either directly or via a small intermediate container, to a heated pump and is brought to the atomising pressure by this pump. Any components of the apparatus located between the screw and the atomising device, as a precautionary measure, should only be heated to a few degrees above the melting point. The total residence time in the liquid phase should not exceed 20 minutes and desirably throughout the melting device such that 95% of any batch of phenacetin is passed through the device within 15 minutes.

The solidification of the atomized phenacetin takes place in a known manner in a gas, such as air, nitrogen, a inert gas or carbon dioxide, or a liquid such as water. When solidified in a gas, the product is obtained in its final form while when solidified in a liquid, it must be subsequently dried. As will be seen from FIGS. 3A, 3B, 4A and 4B the surfaces of crystalline phenacetin are substantially less structured and have a comparably more uniform surface. The spherical-granulate particle on the other hand shows a cracked surface which, under the stronger magnification of FIG. 4B, reveals itself to be fissured and structured. The cracks presumably are stress cracks, produced upon the cooling of the molten material and can be influenced by the spraying and cooling conditions.

The spherical phenacetin granules thus obtained in contrast to crystalline phenacetin, can be tableted direct; i.e., after simple admixture with customary tableting auxiliaries, it can be molded on high output tableting presses to yield tablets having good mechanical properties.

When the ultimate strength of tablets (two fractions of 250/500 μm and 63/160 μm, for each of phenacetin crystals and phenacetin spherical granules) is measured as a function of the pressure of the upper punch, there can be noted an initial increase in the strength with an increase in the compacting pressure. After a critical maximum compacting pressure has been reached, all the tablets show lamination and a tendency towards capping. In the low-pressure range (below 40 MN/M$^2$), tablets of phenacetin crystals exhibit higher strength than tablets of phenacetin spherical granules. In the case of crystals, the compacting pressure for the 63/160 μm fraction cannot be increased beyond about 35 MN/M$^{-2}$ (about 350 kg/cm$^2$) without extensive lamination of the tablets occurring. In the case of the 250/500 μm fraction, it cannot be increased beyond about 45 MN/M$^{-2}$ (about 450 kg/cm$^2$). The maximum strength of tablets of phenacetin crystals lies in the range from just below 2 to just above 2 kg.

In the case of the coarse fraction (250/500 μm) of the spherical granules, the maximum strength of the tablets which can be obtained is 1½ times as great as that of crystals. The difference is even clearer in the case of the fine fraction. With the 63/160 μm fraction of the spherical granules, a 2½ times greater strength could be obtained than is observed for the corresponding fraction of the crystal.

The influence of the compacting pressure on the porosity of the tablet of phenacetin crystals and phenacetin spherical granules of the same screen fractions can also be seen. With an increase in the pressure, the material is more strongly compacted in the form of the tablet compacts, while the porosity decreases. For both crystal fractions, critical limit values of porosity are reached at a relatively low compacting pressure (around 40 MN/M$^2$) and further increase in pressure results in lamination of the tablets. Phenacetin spherical granules can be compacted at substantially higher pressure (about 80 MN/M$^2$) before lamination occurs in the tablet. Thus this material can be compacted to substantially lower values of porosity. When comparing the two fine fractions, a porosity of about 17% is obtained for phenacetin crystals and a porosity of about 8% for the spherical granules. With the crystals and spherical granules, stronger compacting and therefore lower porosity is obtained in each case with the coarser fraction than when employing a comparable compacting pressure with the finer fraction.

Typical tablets are prepared, for example, by using melt-sprayed spherical phenacetin granules in which 80% by weight have a particle size range of from about 20 to about 500 μm, adding 5–40% of micro-crystalline cellulose, 5–30% of starch and 0.05–1% of highly disperse silica (the percentages in each case being by weight, relative to phenacetin), mixing these constituents and compressing on a suitable tableting machine.

The following examples will serve to further typify the invention without being a limitation on the scope thereof. Examples 1–4 describe the preparation of granules. Example 5 is a comparative example utilizing crystalline phenacetin and Examples 6–8 describe tablets which were produced by direct compressing that is to say without dry granulation or moist granulation. The comparison of the results with crystalline phenacetin and melt-sprayed spherical phenacetin granules clearly shows that when using the granules end products with substantially improved properties result, in addition to the technical advantages provided by direct tableting compared to conventional working with crystalline phenacetin.

The tableting machines used in Examples 5–8 included various customary rotary machines and also high speed rotary machines.

EXAMPLE 1

Crystalline phenacetin was fused in an intermeshing twin screw device in which the screws rotate in the same direction, having a 32 mm external screw diameter, 17 mm root diameter and 770 mm screw length, with wall temperatures of 190° C. The residence time was 3.2 minutes in the screw and the throughput rate was 8 kg/hour. The melt was atomized at temperatures of about 140°, by means of a piston pump, with a vortex chamber nozzle in air at 20° C. The total residence time during which the product was exposed to heat was 13 minutes. The product was of requisite purity according to USP XVIII, and had the following particle size distribution:

10% < 126 μm
50% < 242 μm
90% < 332 μm

It was very free-flowing and non-dusting.

EXAMPLE 2

Crystalline phenacetin was fused in the twin screw described in Example 1, at wall temperatures of 210° C, using a residence time of 1.4 minute in the screw. The throughput rate was 18 kg/hour. The material was atomized at temperatures of about 140° C by means of a piston pump with a vortex chamber nozzle, in air at 20° C. The total residence time of the product was 6 minutes. The product conformed to the purity requirements of USP XVIII and had the following particle size distribution:

10% < 80 μm

50% < 160 μm
90% < 212 μm

EXAMPLE 3

Crystalline phenacetin was fused in the twin screw described in Example 1, at wall temperatures of 270° C. The residence time in the screw was 1 minute and the throughput rate was 26 kg/hour. The melt was atomized at temperatures of about 140° C by means of a piston pump with a vortex chamber nozzle, in air at 20° C. The total residence time during which the product was exposed to heat was 4 minutes. The solidified product had the requisite purity and the following particle size distribution:

10% < 91 μm
50% < 168 μm
90% < 247 μm

EXAMPLE 4

Crystalline phenacetin was fused in the twin screw described in Example 1, at wall temperatures of 210° C. The residence time in the screw was 1.5 minute. The throughput rate was 17 kg/hour. The melt was atomized at a temperature of 142° C by means of a piston pump, with a vortex chamber nozzle, in water at 20° C. The total residence time during which the product was exposed to heat was 6 minutes. The solidified and dried product had the requisite purity and the following particle size distribution:

10% < 38 μm
50% < 104 μm
90% < 230 μm

EXAMPLE 5

(Comparative)

| Crystalline phenacetin | 500 g |
| --- | --- |
| Micro-crystalline cellulose | 50 g |
| Maize starch | 28 g |
| Highly disperse silica | 2 g |

The mixed constituents are converted to tablets weighing 580 mg on a 20-stamp rotary press with one compression station, at a machine output of 25,000 tablets per hour.

The tablets have a low hardness and show marked layering and capping.

The example confirms statements in the literature that crystalline phenacetin cannot be compressed directly into tablets.

EXAMPLE 6

| Melt-sprayed phenacetin | 500 g |
| --- | --- |
| Micro-crystalline cellulose | 50 g |
| Maize starch | 28 g |
| Highly disperse silica | 2 g |

As a result of replacing the crystalline phenacetin by melt-sprayed phenacetin, tableting under the same conditions as in Example 5 gives tablets which show no layering, no capping and good hardness. The tablets of Example 5 have a hardness of 1–1.5 kg while the tablets of Example 6 have a hardness of 5–6 kg.

EXAMPLE 7

| Melt-sprayed phenacetin | 250 g |
| --- | --- |

-continued

| Caffeine | 50 g |
| --- | --- |
| Micro-crystalline cellulose | 30 g |
| Maize starch | 19 g |
| Highly disperse silica | 1 g |

A mixture of the constituents in the stated ratios is converted to tablets weighing 350 mg on a high speed press. Tablets of hardness 3–4 kg, which show no capping and no layering, are obtained at an output of 100,000–150,000 tablets per hour.

EXAMPLE 8

| Melt-sprayed phenacetin | 250 g |
| --- | --- |
| Caffeine | 50 g |
| Micro-crystalline cellulose | 30 g |
| Maize starch | 18.7 g |
| Highly disperse silica | 10 1 g |
| Magnesium stearate | 0.3 g |

The composition of Example 8 differs from that of Example 7 in that magnesium stearate is added as lubricant. The addition of lubricant can largely be omitted if the desired tablet is flat faced and has no marks imprinted in it. If the melt-sprayed phenacetin is replaced by crystalline phenacetin in Examples 7 and 8, tablets of hardness 0.5–1 kg and which show severe capping are obtained.

The superiority of the melt-sprayed phenacetin granules over crystalline phenacetin manifests itself not only in conjunction with further additives, as in the preceding examples 6 to 8, but also when the material is pressed by itself, without additives. The maximum achievable crushing strength of a test tablet of 20 mm diameter and weighing 2 g is approximately 1.9 kg for crystalline phenacetin and approximately 4.4 kg for the melt-sprayed phenacetin according to the invention. In these experiments, the same particle size range (6314 160 μm) and the same compressing speed (4 strokes/minute with a reciprocating tableting machine) were used for both types of phenacetin.

What is claimed is:

1. A process for preparing melt-sprayed spherical phenacetin granules which comprises passing crystalling phenacetin through a melting device having heated surfaces maintained at temperatures of from 150° to 300° C at such a rate that the total residence time of the molten phenacetin in the melting device does not exceed 20 minutes and the average residence time does not exceed 10 minutes, and atomizing the melted phenacetin thus produced.

2. A process according to claim 1 wherein the melting device comprises a plurality of intermeshing self-cleaning screws.

3. A process according to claim 2 wherein the melting device comprises two like intermeshing self-cleaning screws arranged in a housing for rotation in the same direction and having clearances between the screw flanks and between the screw crests and the housing of less than $30 \times 10^{-3}$ times the diameter of the screw.

4. A process according to claim 4 wherein the phenacetin is heated to a temperature not more than 10° C above its melting point.

5. A process according to claim 4 wherein the phenacetin is fused by passage through a melting chamber having walls maintained at a temperature of from 150° to 300° C at such a rate that the phenacetin is in molten state no more than 10 minutes.

6. Substantially spherical melt-sprayed granules consisting essentially of pure phenacetin produced in accordance with the process of claim 1.

7. Spherical melt-sprayed granules of phenacetin according to claim 6 in which about 80% by weight have particle sizes of from about 20 to about 500 μm.

8. In the process of preparing compressed pharmaceutical tablets containing phenacetin produced in accordance with the process of claim 1 as a therapeutic agent the improvement which comprises tableting a composition in which the phenacetin is in the form of substantially spherical melt-sprayed granules of pure phenacetin.

9. The process according to claim 8 wherein about 80% by weight of said granules have particle sizes of from about 20 to about 500 μm.

10. A compressed pharmaceutical tablet comprising phenacetin as a therapeutic agent wherein the phenacetin which is compressed is in the form of substantially spherical melt-sprayed granules produced in accordance with the process of claim 1.

11. A tablet according to claim 10 which additionally contains at least one filler and at least one binder.

12. A tablet according to claim 11 wherein the filler includes at least one member selected from the group consisting of an edible carbohydrate, mannitol or silica.

13. A tablet according to claim 12 wherein the filler is starch and highly dispersed silica.

14. A tablet according to claim 12 which additionally contains a lubricant.

15. A tablet according to claim 10 which additionally contains caffeine.

* * * * *